(12) United States Patent
Yamada et al.

(10) Patent No.: US 7,064,320 B2
(45) Date of Patent: Jun. 20, 2006

(54) MASS CHROMATOGRAPH

(75) Inventors: Masuyoshi Yamada, Ichikawa (JP); Izumi Waki, Tokyo (JP); Hideo Kasima, Kokubunji (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/071,345

(22) Filed: Mar. 4, 2005

(65) Prior Publication Data

US 2006/0054806 A1    Mar. 16, 2006

(30) Foreign Application Priority Data

Sep. 16, 2004    (JP) ............................. 2004-269112

(51) Int. Cl.
*H01J 49/26* (2006.01)
*G01N 27/62* (2006.01)

(52) U.S. Cl. ...................... 250/288; 250/281; 250/282; 250/423 R (58) Field of Classification Search ................ None
See application file for complete search history.

(56) References Cited

U.S. PATENT DOCUMENTS 6,686,592 B1 *    2/2004    Sakairi et al. ............... 250/324
6,852,970 B1 *    2/2005    Yamada et al. ............. 250/288

FOREIGN PATENT DOCUMENTS

| JP | 6-310091 | 4/1993 |
|----|----------|--------|
| JP | 9-15207 | 6/1995 |
| JP | 11-295269 | 4/1998 |
| JP | 2001-93461 | 9/1999 |

OTHER PUBLICATIONS

Good, A., et al., "Ion-Molecule Reactions in Pure Nitrogen and Nitrogen Containing Traces of Water at Total Pressures 0.5-4 torr. Kinetics of Clustering Reactions Forming H ($H_2O$)", The Journal of Chemical Physics, vol. 52, No. 1, Jan. 1970, pp. 212-221.

* cited by examiner

*Primary Examiner*—Nikita Wells
(74) *Attorney, Agent, or Firm*—Reed Smith LLP; Stanley P. Fisher, Esq.; Juan Carlos A. Marquez, Esq.

(57) ABSTRACT

A mass spectrometer has an atmospheric pressure chemical ionization source that includes a first ionization portion including a needle electrode, for generating a primary ion by discharge of the needle electrode a primary ion introduction aperture, and a second ionization portion including an introduction aperture, for generating a sample ion by the reaction between the primary ion and the sample gas introduced from an end of a column of gas chromatography, a sample ion movement aperture; and a mass analysis portion; wherein the end is arranged at a position satisfying the relation $r \leq 2R$ where R is a radius of an inner diameter of the aperture and r is a distance between an axis connecting the center of the aperture and the center of the aperture, and the end.

13 Claims, 7 Drawing Sheets

MASS CHROMATOGRAPH

INCORPORATION BY REFERENCE

The present application claims priority from Japanese application JP 2004-269112 filed on Sep. 16, 2004, the content of which is hereby incorporated by reference into this application.

BACKGROUND OF THE INVENTION

1. Field of the Invention

This invention relates to an atmospheric pressure chemical ionization mass spectrometry for analyzing a sample gas separated by gas chromatography.

2. Description of the Related Art

In the description to follow, gas chromatography will be abbreviated as "GC", a mass spectrometer, as "MS", an apparatus including the combination of the gas chromatography and the mass spectrometer, as "GC/MS", an atmospheric pressure chemical ionization source, as "APCI source", an atmospheric pressure chemical ionization mass spectrometer (apparatus including the combination of APCI and MS), as "APCI/MS", a chemical ionization source, as "CI source", an electron impact ion source, as "EI source", and an apparatus including the combination of the gas chromatography and the atmospheric pressure chemical ionization mass spectrometer, as "GC/APCI/MS".

GC/MS is a known analytic technology. APCI/MS is an apparatus that ionizes trace components in a mixed sample and detects them with a high level of sensitivity by using an ion-molecule reaction. This apparatus has been utilized for the analysis of the trace components contained in environmental samples and living body samples. A report of a high sensitivity analytical apparatus including the combination of GC and APCI/MS, for analyzing various trace impurities inclusive of semiconductor specific gases (refer to JP-A-9-15207) and a report of an analytical apparatus including the combination of GC and APCI/MS, for analyzing trace impurities in gases for the measurement of the trace impurities of ppb to sub-ppb levels in various high impurity gases (refer to JP-A-11-295269) have been made. Another report (refer to JP-A-6-310091) is known that separates an ion generation portion and a sample gas introduction portion and efficiently transports ions into apertures so that trace impurities can be measured with a high sensitivity and stably for a long time even for those semiconductor material gases such as monosilane and disilane that are likely to invite contamination inside an ion source.

According to JP-A-9-15207, the sample gas separated in a column of the GC is mixed with a carrier gas and is then introduced to an APCI source through a line. The flow rate of the carrier gas flowing through the line is set to a minimum flow rate that can keep the atmospheric pressure inside a discharge space of the APCI source for the purpose of high sensitivity analysis. An orifice is disposed so that the discharge space can be kept steadily and easily at the atmospheric pressure and the flow rate of an exhaust line can be regulated to the minimum flow rate.

According to JP-A-11-295269, there is an introduction system extending to APCI/MS through GC and a makeup flow passage connected to an outflow passage from GC is disposed. The reference puts the following description:

"The flow rate of the sample gas introduced into APCI/MS is generally from hundreds of mL (milliliters)/min to several L/min. The flow rate of the carrier gas of GC is generally 20 to 50 mL/min. It is therefore necessary to add a corresponding amount of a makeup gas from the makeup passage to the outflow gas from GC. Because this makeup gas dilutes the impurities as the assumed objects, however, its flow rate must be reduced as much as possible. To improve the sensitivity of the impurities in the analysis through GC, therefore, it is preferred to minimize the flow rate of the sample gas introduced into APCI/MS such as about 300 mL/min."

JP-A-6-310091 puts the following description:

". . . includes an ion generation portion as an area for generating a primary ion, having an introduction port of a primary ion generation gas and ionization means, a sample introduction portion as an area into which the sample gas is introduced, a mixing portion in which the primary ion supplied with the primary ion generation gas from the ion generation portion is mixed with the sample gas and ions of an object material in the sample gas are generated by an ion-molecule reaction, and a mass analysis portion which is held under high vacuum and in which the ion introduced from the mixing portion through an aperture is subjected to mass separation, wherein at least one of means for transporting the ion to the aperture by adding an electric field by an electrode disposed in the mixing portion, means for constituting the ion generation portion and the sample introduction portion into a double wall tube and making the flow of the primary ion generation gas and the flow of the sample gas parallel to each other in the mixing portion, and means for discharging the gas reaching the aperture in a direction extending along a surface having the aperture is added so as to increase a detection ion amount".

In the column of "Prior Art", JP-A-6-310091 reads as follows:

"The primary ion is injected with the primary ion generation gas under the atmospheric pressure and the primary ion is mixed with the sample gas at the atmospheric pressure ahead of the aperture of the mass analysis portion. The ion of the object material is generated by the ion-molecule reaction. Because the ion generation portion and the sample introduction portion are separated in APCI/MS, the ion generation portion is not contaminated even when a gas flowing out from GC and LC (liquid chromatograph) is used as the sample gas and ionization can be carried out stably for a long time".

Ionization of the sample gas by chemical ionization in air is well known (refer to "The Journal of Chemical Physics", Vol. 52, 212–221(1970)).

In JP-A-9-15207, the sample gas separated in the column of GC is mixed with the carrier gas and is introduced into the APCI source through the line. In JP-A-11-295269, the outflow gas from GC is introduced into APCI/Ms after the makeup gas is added from the makeup passage. Therefore, the outflow gas from GC is diluted. Because ionization of the sample described in "Prior Art" in JP-A-6-310091 is conducted at the atmospheric pressure, the outflow gas from GC is diluted, too. Even when the outflow gas from GC is allowed to flow through the sample introduction portion in the construction for increasing the detection ion amount in JP-A-6-310091, the outflow gas is diluted by the primary ion generation gas in the mixing portion. As described above, the prior art technologies do not sufficiently take dilution into consideration when the outflow gas from GC is introduced into the APCI source, and are not free from the problem of the drop of the sensitivity.

The analysis by GC/MS is suitable for separation analysis of a plurality of components contained in a mixed sample, particularly for separation analysis of components having high volatility. The ion source used for GC/MS generally includes a CI source and an EI source. These ion sources are used for ionization under vacuum of about 0.1 torr to several torr. The sample gas separated by GC is introduced into the ion source under this vacuum. However, when the sample contains a large number of impurities, the impurities are adsorbed to the wall of the ion source and to constituent components and remain inside the ion source. Consequently, the ion source is contaminated and an S/N ratio gets decreased. Therefore, maintenance such as frequent cleaning of the ion source is necessary and hinders efficient analysis.

When the APCI source is used for the ion source, on the other hand, ionization of the sample is conducted at the atmospheric pressure and a differential exhaust portion for transporting the ion from the ion source to the mass analysis portion under vacuum is disposed. The ion from the ion source is introduced into the vacuum portion through an ion introduction aperture having a diameter of about 0.1 to about 0.5 mm$\phi$. To keep stable duration of corona discharge, a gas (primary ion generation gas (discharge gas)) of a flow rate of about 0.1 to about 1 L/min must be caused to flow steadily to the ion source and the gas flow rate flowing through the ion introduction aperture is about 0.1 to about 1 L/min.

Because the flow rate from GC is several to dozens of mL/min, the gas from GC is diluted by the primary ion generation gas that is caused to flow to the ion source. However, the problem of the drop of sensitivity occurs when the gas from GC is merely mixed with the primary ion generation gas.

SUMMARY OF THE INVENTION

It is an object of the invention to provide an APCI source not easily contaminated, and a mass spectrometer and a mass spectrometry including the combination of a gas chromatography using this APCI source and capable of high sensitivity analysis without being affected by dilution of a sample gas by a primary ion generation gas with an atmospheric pressure ionization mass spectrometer.

A typical construction of the mass spectrometer (GC/APCI/MS) according to the invention will be explained. The APCI source includes a first ionization portion for generating a primary ion from a primary ion generation gas by corona discharge generated by a voltage applied to a needle electrode disposed inside the first ionization portion, and a second ionization portion for generating a sample ion by an ion-molecule reaction between the sample gas directly introduced from an end of a GC column and the primary ion sent from the first ionization portion, having an aperture at the end of the GC column disposed therein.

The sample gas separated in the GC column contains a single component completely separated or a plurality of components not completely separated. The first ionization portion and the second ionization portion are separated from each other by a lead-out electrode having a primary ion introduction aperture through which the primary ion passes. The primary ion generation gas introduced into the second ionization portion passes through the primary ion introduction aperture, flows to the tip end of the needle electrode and is exhausted from the first ionization portion. The sample ion generated in the second ionization portion is introduced into the mass analysis portion through the sample ion movement aperture, the differential exhaust portion and the sample ion introduction aperture and is subjected to mass analysis.

The sample gas is directly introduced from a position in the proximity of an axis connecting the center of the primary ion introduction aperture through which the primary ion passes and the center of the sample ion movement aperture through which the sample ion moves, into the second ionization portion from the aperture at the end of the GC column. The center of the aperture at the end of the GC column is arranged at the position that is substantially equidistant from the center of an ion outlet of the primary ion introduction aperture and from the center of an ion inlet of the sample ion movement aperture and satisfies the relation $r \leqq 2R$ where R is a radius of the primary ion introduction aperture and r is a distance from the axis connecting the center of the primary ion introduction aperture to the center of the sample ion movement aperture.

The sample gas that is directly introduced with the carrier gas from the aperture at the end of the GC column into the second ionization portion under the state where it is not diluted flows to the primary ion introduction aperture and to the sample ion movement aperture at substantially the same flow rate along the axis connecting the center of the primary ion introduction aperture to the center of the sample ion movement aperture.

The retention time in which the primary ion and the sample molecule coexist in the field of the ion-molecule reaction as the field in which the primary ion and the sample molecule react with each other becomes long and a sufficient time for the progress of the ion-molecule reaction can be secured. In consequence, the sample molecule can be efficiently ionized, the generation amount of the sample ion increases and the sensitivity can be improved.

Because the sample gas flows through the primary ion introduction aperture and the sample ion movement aperture while being diluted by the primary ion generation gas, the APCI source (first ionization portion, second ionization portion, needle electrode, apertures) is not contaminated by the impurities contained in the sample gas and the analysis can be carried out at a high sensitivity without being affected by the impurities.

The mass spectrometer (GC/APCI/MS) according to the invention can analyze at a high sensitivity the mixed sample containing large amounts of impurities without contamination of the ion source by the impurities.

The invention can provide an APCI source not generating contamination and a mass spectrometer (GC/APCI/MS) and a mass spectrometry using the APCI source and capable of high sensitivity analysis without being affected by dilution of a sample gas by a primary ion generation gas.

The invention employs a construction in which a sample gas is directly introduced into the field of an ion-molecule reaction capable of ionization with high efficiency and the resulting sample ion is introduced highly efficiently into a mass analysis portion. Therefore, the invention can prevent the drop of sensitivity due to dilution of the sample gas before its introduction into an ion source and contamination of the ion source, and makes it possible to conduct high sensitivity analysis.

The mass spectrometer according to preferred embodiments of the invention will be explained in detail with reference to the accompanying drawings.

Other objects, features and advantages of the invention will become apparent from the following description of the embodiments of the invention taken in conjunction with the accompanying drawings.

DESCRIPTION OF THE EMBODIMENTS

First Embodiment

Figure 1:
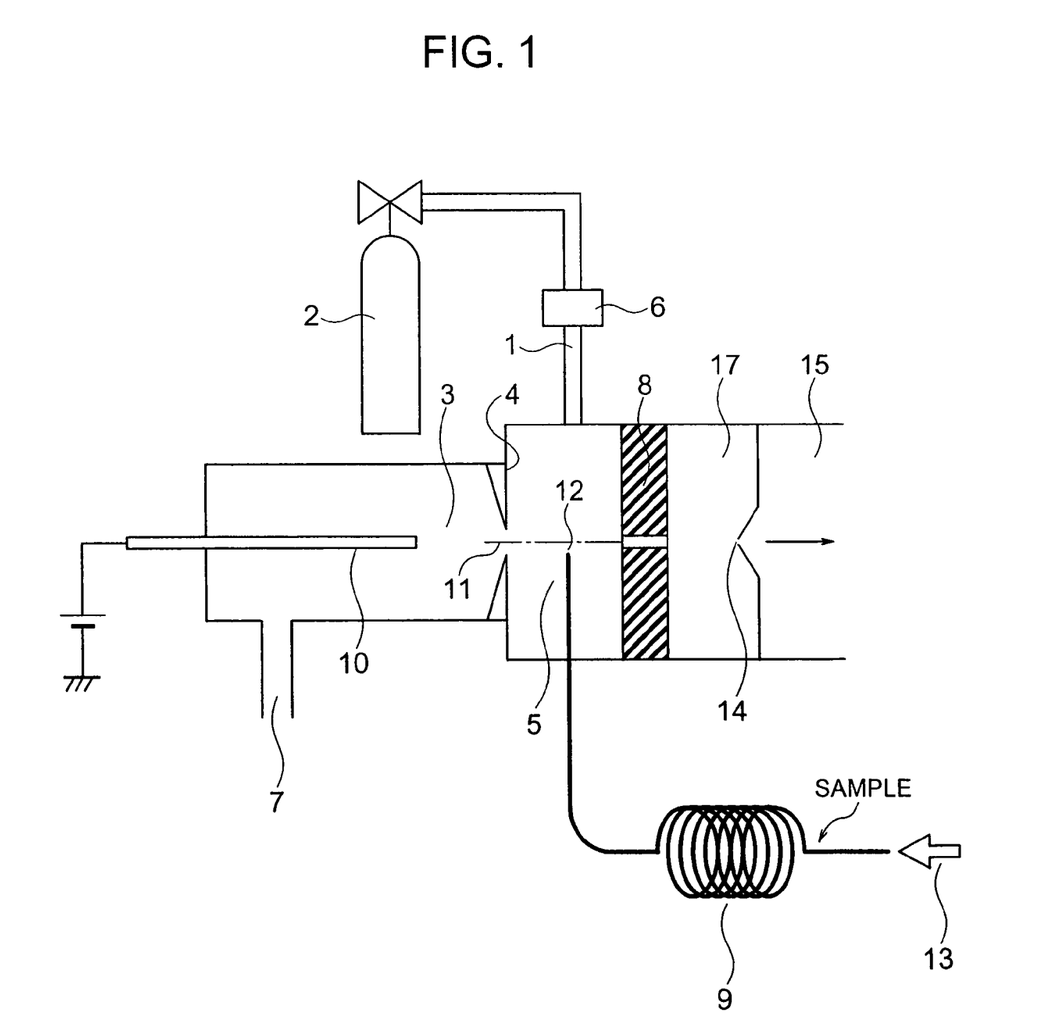
FIG. 1 is a sectional view showing a construction of a mass spectrometer according to a first embodiment of the invention.

FIG. 1 is a sectional view showing a construction of a mass spectrometer according to a first embodiment of the invention. This mass spectrometer (GC/APCI/MS) is a high sensitivity apparatus that ionizes sample molecules (sample gas) separated by a GC column by an APCI source and analyzes the mass.

A first ionization portion 3 and a second ionization portion 5 are separated from each other by a first partition (lead-out electrode 4) having a primary ion introduction aperture 11 through which a primary ion passes. The second ionization portion 5 is an area that is interposed by the first partition and a second partition that has a sample ion movement aperture 8 through which a sample ion of a sample gas generated by the reaction between the sample molecule and the primary ion (hereinafter called "ion-molecule reaction") inside the second ionization portion 5 passes.

The mass spectrometer according to the first embodiment includes the first ionization portion 3, the second ionization portion 5, a differential exhaust portion 17 and a mass analysis portion 15. The first ionization portion 3 and the second ionization portion 5 are separated by the lead-out electrode 4 having the primary ion introduction aperture 11 and the second ionization portion 5 and the differential exhaust portion 17 are separated by a wall having the sample ion movement aperture 8. The differential exhaust portion 17 and the mass analysis portion 11 are separated by a wall having an ion introduction aperture 14. The primary ion introduction aperture 11 is an aperture through which the primary ion generated in the first ionization portion 3 moves and the sample ion movement aperture 8 is an aperture through which the sample ion generated in the second ionization portion 5 moves. The ion introduction aperture 14 is an aperture for introducing the sample ion into the mass analysis portion 15. The sample ion moves into the mass analysis portion 15 through the sample ion movement aperture 8, the differential exhaust portion 17 and the ion introduction aperture 14.

The needle electrode 10 is arranged inside the first ionization portion 3 as a corona discharge portion and a primary ion generation gas exhaust piping 7 is connected. The primary ion generation gas exhaust piping 7 is connected to the first ionization portion 3 at a position far from the lead-out electrode 4 (position on the root side of needle electrode 10) on the opposite side to the tip end of the needle electrode 10.

A primary ion generation gas introduction piping 1 for supplying a primary ion generation gas from a gas cylinder 2 is connected to the second ionization portion 5. The primary ion generation gas from the gas cylinder 2 is introduced through the primary ion generation gas introduction piping 1 into the second ionization portion 5 while its flow rate is regulated by a mass flow controller 6. The primary ion generation gas is preferably the one that does not impedes ionization of the sample gas introduced from the aperture 12 at the end of the GC column 9 into the second ionization portion 5, such as air, nitrogen, or helium and argon having low ionization efficiency. A high voltage is applied to the needle electrode 10 and the primary ion generation gas is ionized due to corona discharge to generate the primary ion.

The primary ion generation gas introduced into the second ionization portion 5 and the sample gas flow along an axis (indicated by one-dot-chain line in FIG. 1) connecting the center of the primary ion introduction aperture 11 to the center of the sample ion movement aperture 8 into the first ionization portion 3 through the primary ion introduction aperture 11 and into the differential exhaust portion 17 through the sample ion movement aperture 8. The primary ion flows also into the second ionization portion 5 along the axis indicated by one-dot-chain line in FIG. 1. Therefore, the field of the ion-molecule reaction in which the ion-molecule reaction proceeds is an area in the proximity of the axis in which the primary ion and the sample molecule coexist and which is indicated by one-dot chain line in FIG. 1.

The flow rate of the primary ion generation gas to be introduced into the second ionization portion 5 is the balance obtained by subtracting the flow rate of the sample gas introduced from the aperture 12 at the end of the GC column 9 into the second ionization portion 5 from the sum of the flow rate of the gas exhausted from the primary ion generation gas exhaust piping 7 and the flow rate of the gas flowing out from the sample ion movement aperture 8 into the differential exhaust portion 17. The mass flow controller 6 arranged in the primary ion generation gas introduction piping 1 or a mass flow controller (not shown) arranged in the primary ion generation gas exhaust piping 7 regulates the flow rate of the primary ion generation gas.

The sample (mixed sample) is introduced with a carrier gas 13 into one of the ends (inlet) of the GC column 9 and is separated. A liquid sample is injected into the inlet of the GC column 9 or a gas of components adsorbed to a solid and desorbed by heating is introduced into the GC column 9. The carrier gas 13 allowed to flow into the GC column 9 is preferably helium or nitrogen as an inert gas. Preferably, the mass flow controller or a pressure controller (not shown) controls the flow rate of the carrier gas 13 to a constant flow rate.

The center of the aperture 12 at the end (other end) of the GC column 9 is arranged in the proximity of the axis indicated by one-dot-chain line in FIG. 1. Because the aperture 12 at the end of the GC column 9 for introducing the sample gas (which flows through the GC column with the carrier gas and contains a single component separated completely or a plurality of components not completely separated) separated by the GC column 9 is arranged in the proximity of the axis indicated by one-dot-chain line in FIG. 1, dilution of the sample as by the primary ion generation gas can be prevented and high sensitivity can be achieved. The detailed explanation of the position at which the center of the aperture 12 at the end of the GC column 9 is arranged will be given later.

To increase the generation amount of the sample ion by the ion-molecule reaction and to accomplish a high sensitivity, it is necessary to secure the field of the ion-molecule reaction as long as possible, to extend the retention time of the coexistence of the primary ion and the sample molecule and to secure the time in which the ion-molecule reaction proceeds. To this end, it is important to introduce the sample gas into the position in the proximity of the axis indicated by one-dot-chain line in FIG. 1 lest the sample gas introduced from the aperture 12 at the end of the GC column 9 into the second ionization portion 5 is diluted by the primary ion generation gas inside the second ionization portion 5.

In the second ionization portion 5, the lead-out electrode 4 leads out the primary ion, the sample gas is introduced into the position in the proximity of the axis indicated by one-dot-chain line in FIG. 1 and the sample ion is generated by the ion-molecule reaction. The sample gas introduced from the aperture 12 at the end of the GC column 9 is diluted inside the second ionization portion 5 and is exhausted from the sample ion movement aperture 8 and the primary ion introduction aperture 11.

When the center of the aperture 12 of the GC column 9 is too close to the sample ion movement aperture 8, the sample gas is exhausted almost fully from the sample ion movement aperture 8. At this time, the retention time in which the primary ion and the sample molecule coexist becomes short in the field of the ion-molecule reaction, a sufficient time for the ion-molecule reaction cannot be secured, the generation amount of the sample ion becomes small and the sensitivity drops.

When the center of the aperture 12 of the GC column 9 is too close to the primary ion introduction aperture 11, the sample gas is exhausted almost fully from the primary ion introduction aperture 11. At this time, too, the retention time in which the primary ion and the sample molecule coexist becomes short in the field of the ion-molecule reaction, a sufficient time for the ion-molecule reaction cannot be secured, the generation amount of the sample ion becomes small and the sensitivity drops in the same way as described above.

To increase the generation amount of the sample ion and to improve the sensitivity, it is important to secure the retention time in which the primary ion and the sample molecule coexist in the field of the ion-molecule reaction and to secure a sufficient time in which the ion-molecule reaction proceeds. When the center of the aperture 12 at the end of the GC column 9 is arranged at a position substantially equidistant from the center of the ion outlet of the primary ion introduction aperture 11 and from the center of the ion inlet of the sample ion movement aperture 8, the sample gas introduced from the aperture 12 at the end of the GC column 9 is discharged with good balance from the primary ion introduction aperture 11 and the sample ion movement aperture 8. Consequently, the retention time in which the primary ion and the sample molecule coexist can be extended and the sufficient time for the progress of the ion-molecule reaction can be secured. As a result, the generation amount of the sample ion can be increased and the sensitivity can be improved. The process in which the sample ion is generated will be later explained in detail.

Incidentally, the tip end of the needle electrode 10, the center of the primary ion introduction aperture 11, the center of the sample ion movement aperture 8 and the center of the ion introduction aperture 14 are arranged on the same axis in the construction of the first embodiment but they can be so arranged as to be deviated from one another. When they are arranged in deviation, it is possible to prevent the neutral molecule from mixing into the mass analysis portion 15 and to reduce the noise resulting from the neutral molecule.

The sample ion generated at the position in the proximity of the axis indicated by one-dot-chain line in FIG. 1 inside the second ionization portion 5 is caused to flow through the sample ion movement aperture 8 by the potential applied between the sample ion movement aperture 8 and the ion introduction aperture 14, is introduced in the direction indicated by arrows into the mass analysis portion 15 exhausted to high vacuum by an exhaust system not shown in the drawing through the ion introduction aperture 14, and mass analysis of the sample ion is made. Mass spectrometers such as a quadrupole mass spectrometer, an ion trap mass spectrometer, an ion trap TOF (time of-flight) mass spectrometer, magnetic section mass spectrometer, etc, can be applied to the mass analysis portion 15.

The primary ion generation gas flowing through the sample ion movement aperture 8 and the sample gas are exhausted by an exhaust system, not shown, for exhausting the differential exhaust portion 17.

When the aperture diameter of the sample ion movement aperture 8 is 0.25 mmφ and the degree of vacuum is 2 Torr in the construction shown in FIG. 1, the second ionization portion 5 is at 760 Torr (atmospheric pressure). Therefore, the flow rate of the gas flowing through the sample ion movement aperture 8 is about 350 mL/min. When the introduction amount of the primary ion generation gas is 1,000 mL/min, the flow rate of the gas flowing out from the primary ion introduction aperture 11 into the first ionization portion 3 is about 650 mL/min.

The sample is separated by the GC column 9 and the sample components so separated are serially introduced with the carrier gas 13 from the aperture 12 at the end of the GC column 9 into the second ionization portion 5. When a capillary GC column 9 having high resolution is used, the flow rate of the carrier gas 13 is several mL/min and the sample gas from the GC column 9 is introduced to the position in the proximity of the axis indicated by one-dot-chain line in FIG. 1. Therefore, the generation amount of the sample ion can be increased. The sample gas flowing into the second ionization portion 5 flows along the axis indicated by one-dot-chain line in FIG. 1 and is sufficiently diluted by the primary ion generation gas passing through the primary ion introduction aperture 11. Consequently, the inner wall of the second ionization portion 5 is not contaminated by impurities contained in the sample gas.

The outline of the ionization process of the sample gas is as follows. The explanation will be given on the case of positive ionization by way of example. Corona discharge is induced between the needle electrode 10 to which a high voltage of about +4 kV is applied and the lead-out electrode 4 to which about +1 kV is applied. When dry air is used for the primary ion generation gas, for example, the primary ion ($N_2^+$ or $N_4^+$) is generated by the reaction of the Expression (1) or (2) (refer to the afore-mentioned "The Journal of Chemical Physics", Vol. 52, 212–221(1970)"):

$$N_2 \rightarrow N_2^+ + e^- \quad (1)$$

$$N_2^+ + 2N_2 \rightarrow N_4^+ + N_2 \quad (2)$$

Because the primary ion introduction aperture 11 having a diameter of about 2 mmφ is formed in the lead-out electrode 4, the resulting primary ion is introduced by the electric field into the second ionization portion 5. The ion of the sample gas (secondary ion: sample ion) is generated inside the second ionization portion 5 by the ion-molecule reaction between the primary ion generated by the corona discharge and the sample gas introduced from the aperture 12 at the end of the GC column 9.

The construction of the first embodiment shown in FIG. 1 is particularly effective when negative ionization of the sample gas is conducted. When negative ionization of the sample gas is conducted by using air for the primary ion generation gas, the primary ion generation gas flows from the needle tip of the needle electrode 10 towards its root and the reaction between the radical NO* resulting from the corona discharge and the primary ion $O_2^-$ can be suppressed. Also, the sensitivity can be improved because $O_2^-$ led out to the second ionization portion 5 efficiently reacts with the sample gas introduced from the aperture 12 at the end of the GC column 9.

Figure 2:
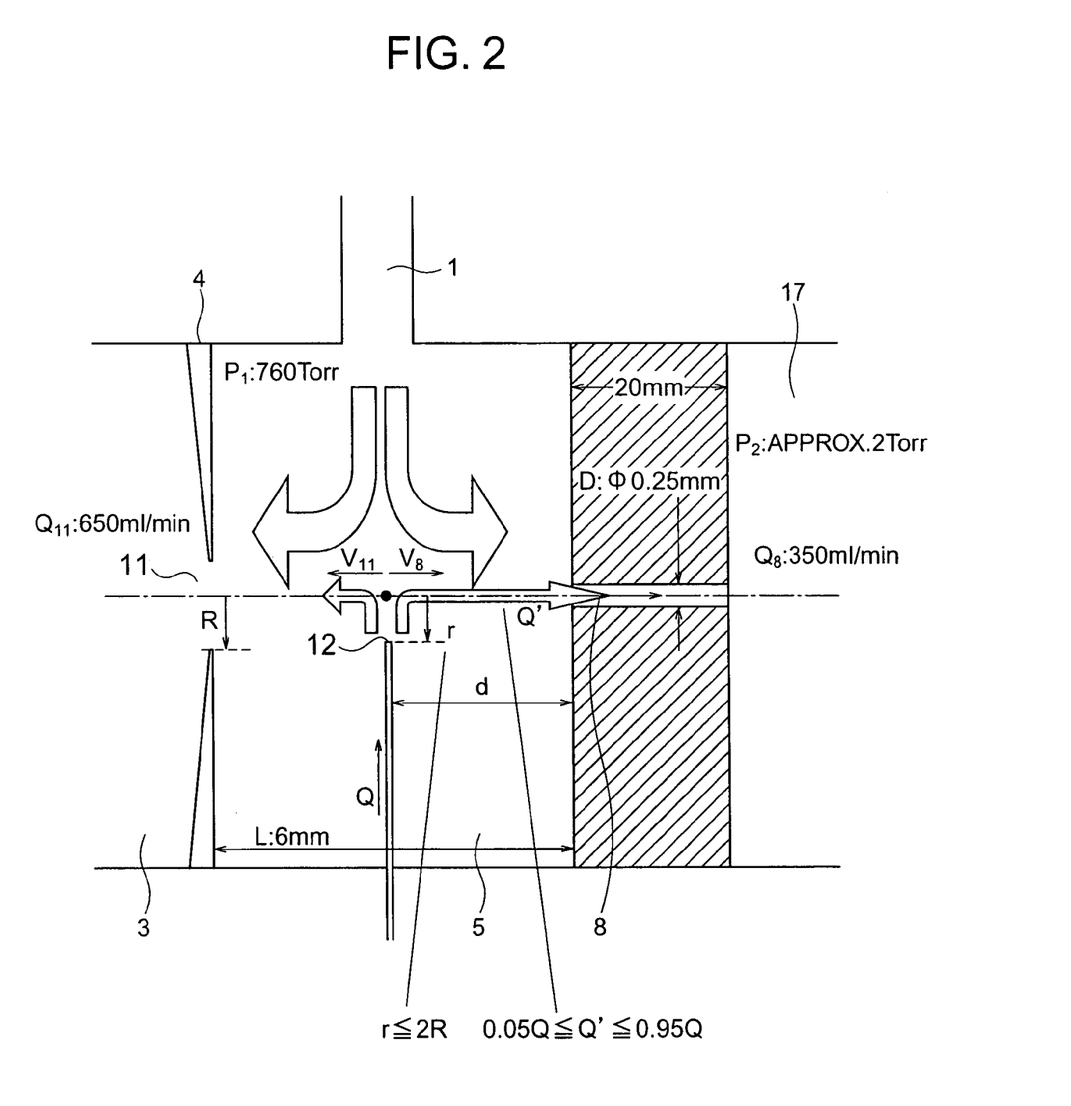
FIG. 2 is a partial enlarged view of FIG. 1 and is an explanatory view showing an arrangement of the center of an aperture 12 at an end of a GC column 9 inside a second ionization portion 5 and the flow of a gas inside the second ionization portion 5.

FIG. 2 is a partial enlarged view of FIG. 1 and explains the center position of the aperture 12 at the end of the GC column 9 and the flow of the gas inside the second ionization portion 5.

When the pressure $P_1$ of the second ionization portion 5 is 760 Torr, the pressure $P_2$ of the differential exhaust portion 17 is 2 Torr, the diameter of the sample ion movement aperture 8 is D=0.25 mmφ and its length is 20 mm, the amount $Q_8$ of the gas that flows into the sample ion movement aperture 8 is about 350 mL/min. The position in the proximity of the axis indicated by one-dot-chain line in FIGS. 1 and 2 is the area in which the concentration of the primary ion generated by the corona discharge is high and when the sample gas is directly injected into this area, a high sensitivity can be achieved.

The construction satisfying the relation r≦2R is preferred when R is the inner diameter (radius) of the primary ion introduction aperture 11 and r is the distance between the center of the aperture 12 at the end of the GC column 9 and the axis indicated by one-dot-chain line. The center of the aperture 12 at the end of the GC column 9 in the direction of the axis indicated by one-dot-chain line in FIGS. 1 and 2 is preferably arranged at the position that can extend the coexistence retention time of the primary ion and the sample molecule in the field of the ion-molecule reaction and can secure the sufficient reaction time.

When the center of the aperture 12 at the end of the GC column 9 is too close to the sample ion movement aperture 8, the sample gas is discharged almost fully from the sample ion movement aperture 8. Because the sample gas is not ionized at this time and is discharged from the primary ion introduction aperture 11, the coexistence retention time of the primary ion and the sample molecule in the field of the ion-molecule reaction becomes short, the sufficient time in which the ion-molecule reaction proceeds cannot be secured, the generation amount of the sample ion decreases and the sensitivity drops in the same way as described above.

When the center of the aperture 12 at the end of the GC column 9 is too close to the primary ion introduction aperture 11, the sample gas is discharged almost fully from the primary ion introduction aperture 11. At this time, too, because the sample gas is not ionized and is discharged from the primary ion introduction aperture 11, the coexistence retention time of the primary ion and the sample molecule in the field of the ion-molecule reaction becomes short, the sufficient time in which the ion-molecule reaction proceeds cannot be secured, the generation amount of the sample ion decreases and the sensitivity drops in the same way as described above.

In other words, to accomplish the high sensitivity, it is necessary to arrange the center of the aperture 12 at the end of the GC column 9 at the position at which the sample gas introduced from the aperture 12 at the end of the GC column 9 can be discharged with good balance from the primary ion introduction aperture 11 and from the sample ion movement aperture 8 inside the second ionization portion 5. When such a construction is employed, the coexistence retention time of the primary ion and the sample molecule in the field of the ion-molecule reaction can be sufficiently extended, the sufficient time for the progress of the ion-molecule reaction can be secured, too, the generation amount of the sample ion can be increased and the sensitivity can be improved.

Preferably, the position from the axis indicated by one-dot-chain line and the center position of the aperture 12 at the end of the GC column 9 in the direction of the axis indicated by one-dot-chain line in FIGS. 1 and 2 are regulated so as to satisfy the relation 0.02Q≦Q'≦0.95Q when Q is the flow rate of the sample gas flowing through the aperture 12 at the end of the GC column 9 and Q' is the flow rate of the sample gas Q discharged to the differential exhaust portion 17 through the sample ion movement aperture 8.

The number of the sample ions generated by the ion-molecule reaction between the sample molecule and the primary ion can be calculated in accordance with the following expression:

Number of sample ions=sensitivity coefficient (A)×
collision cross section (σ)×primary ion density
(I)×reaction time (T)×sample concentration (ρ)  expression (1)

Here, when the distance d of the center position of the aperture 12 at the end of the outlet of the GC column 9 from the ion inlet of the sample ion introduction aperture 8 is changed, A, σ and I remain unchanged in the expression (1) and ρ is constant when the measurement is made under the same sample condition. Therefore, the reaction time T can be estimated in the following way.

A velocity distribution inside the second ionization portion 5 will be considered on the assumption that no disturbance exists in the proximity of the introduction portion of the primary ion generation gas introduced from the primary ion generation gas introduction piping 1. The flow rate of the sample gas introduced from the aperture 12 at the end of the GC column 9 is by far smaller than the flow rate of the primary ion generation gas introduced from the primary ion generation gas introduction piping 1. Therefore, the influences of the introduction of the sample gas on the flow field are neglected. A flow velocity vector at the position spaced apart by the distance d from the center of the ion inlet of the sample ion movement aperture 8 in the proximity of the axis connecting the center of the ion outlet of the primary ion introduction aperture 11 and the center of the ion inlet of the sample ion movement aperture 8 is the sum of a velocity vector $V_8$ due to the gas flow exhausted from the sample ion movement aperture 8 (direction represents the center of sample ion movement aperture 8) and a speed vector $V_{11}$ (direction represents the center of sample ion movement aperture 11) due to the gas flow exhausted from the primary ion introduction aperture 11. The magnitudes of the vectors (flow velocity) are expressed by expression (2) and (3).

$$V_8 = Q_8/2\pi d^2 \qquad \text{expression (2)}$$

$$V_{11} = Q_{11}/(2\pi(L-d)^2) \qquad \text{expression (3)}$$

Here, $Q_8$ and $Q_{11}$ represent the gas flow rates exhausted from the sample ion movement aperture 8 and from the primary ion introduction aperture 11, respectively, and L represents the distance between the center of the sample ion movement aperture 8 and the center of the primary ion introduction aperture 11. Expressions (2) and (3) represent that the flow velocity becomes smaller at positions away from the respective exhaust ports (sample ion movement aperture 8 and primary ion introduction aperture 11).

Let's consider the time T till the sample molecule at the position spaced apart by the distance d from the center of the sample ion movement aperture 8 enters the sample ion movement aperture 8. When the velocity vector $V_{11}$ is negligibly small in the proximity of the sample ion movement aperture 8, for example, that is, when d is smaller than L, only $V_8$ may be taken into consideration as the flow velocity. The time $T_8$ (reaction time) till the sample molecule introduced from the aperture 12 at the end of the outlet of the GC column 9 enters the sample ion movement aperture 8 is calculated into expression 4 by integrating the expression (2).

$$T_8 = (2\pi d^3)/(3Q_8) \qquad \text{expression (4)}$$

Similarly, when the position of the sample molecule is close to the primary ion introduction aperture 11 and d is close to L, only $V_{11}$ may be taken into consideration as the flow velocity and the reaction time $T_{11}$ is calculated into expression (5) by integrating the expression (3).

$$T_{11} = (2\pi(L-d)^3)/(3Q_{11}) \qquad \text{expression (5)}$$

To increase the number of sample ions expressed by expression (1), that is, to improve the sensitivity, the aperture 12 at the end of the outlet of the GC column 9 is preferably arranged at the position that increases the reaction time $T_8$ or $T_{11}$.

Figure 3:
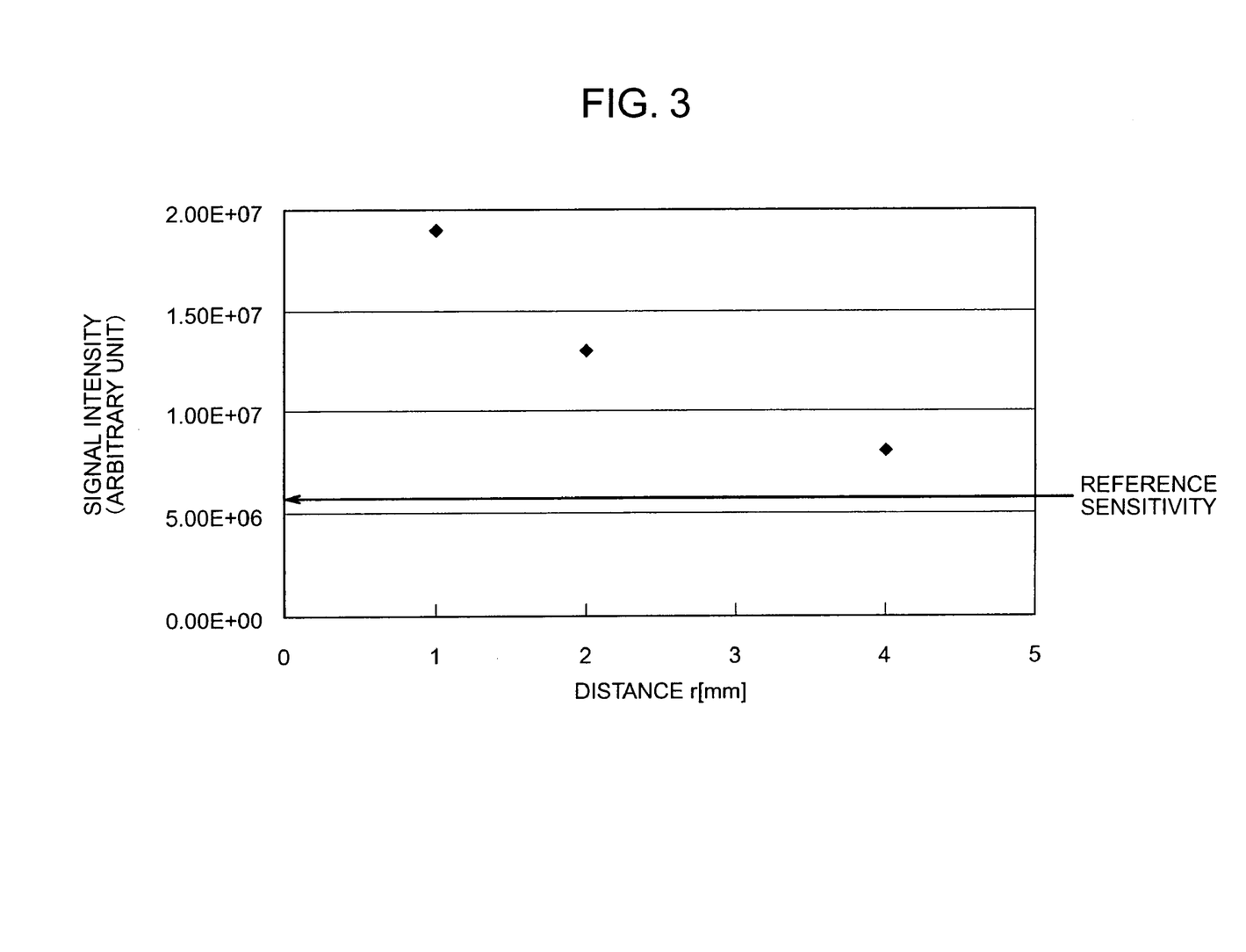
FIG. 3 is a diagram showing a measurement result of a change of a signal intensity by a sample ion detected when a distance r between the center of the aperture 12 at the end of the GC column 9 and an axis indicated by one-dot-chain line in FIGS. 1 and 2 is changed in the construction of the first embodiment.

FIG. 3 shows the measurement result of the change (sensitivity change) of the signal intensity (in arbitrary unit) by the sample ion that is detected when the distance r between the center position of the aperture 12 at the end of the GC column 9 and the axis indicated by one-dot-chain line shown in FIGS. 1 and 2 is changed. In the expression of the ordinate in FIG. 3, the value 2.00E+7 represents $2.00 \times 10^7$. This also holds true of the expression of the ordinate in FIGS. 4 and 7.

Under the measurement condition shown in FIG. 3, measurement is conducted by charging 1 μL of a toluene solution of trichlorophenol (TCP) having a concentration of 1 ppm as a sample into the GC column 9, setting a carrier gas flow rate to 5 mL/min and measuring positive ions by using an ion trap type mass spectrometer. For comparison, FIG. 3 shows, as a reference sensitivity, the signal intensity (in arbitrary unit) measured by charging the same sample into the GC column 9, conducting separation, connecting the aperture 12 at the end of the GC column 9 to the primary ion generation gas introduction piping 1 between the mass flow controller 6 and the second ionization portion shown in FIG. 1, and mixing the separated sample gas flowing out from the aperture 12 at the end of the GC column 9 with the primary ion generation gas that is caused to flow at a rate of 1,000 mL/min through the primary ion generation gas introduction piping 1.

The sensitivity can be improved 3.2 times, 2.2 times and 1.3 times at r=1 mm, 2 mm and 4 mm, respectively, in comparison with the reference sensitivity. It can be understood from this result that the sensitivity becomes lower as the distance r between the center of the aperture 12 at the end of the GC column 9 and the axis indicated by one-dot-chain line shown in FIGS. 1 and 2 becomes greater. It can be understood also from the result shown in FIG. 3 that the signal intensities (in arbitrary unit) measured at r=1 mm, 2 mm and 4 mm satisfying the relation r≦2R=4 mm with respect to the inner diameter of the primary ion introduction aperture 11 (radius R=2 mm (2R=4 mm)) is greater than the reference sensitivity. It has been confirmed that when r≦2R, the sensitivity can be made higher than when the measurement is conducted by merely connecting the aperture 12 at the end of the GC column 9 to the primary ion generation gas introduction piping 1 and mixing the separated sample gas flowing out from the aperture 12 at the end of the GC column 9 with the primary ion generation gas.

Figure 4:
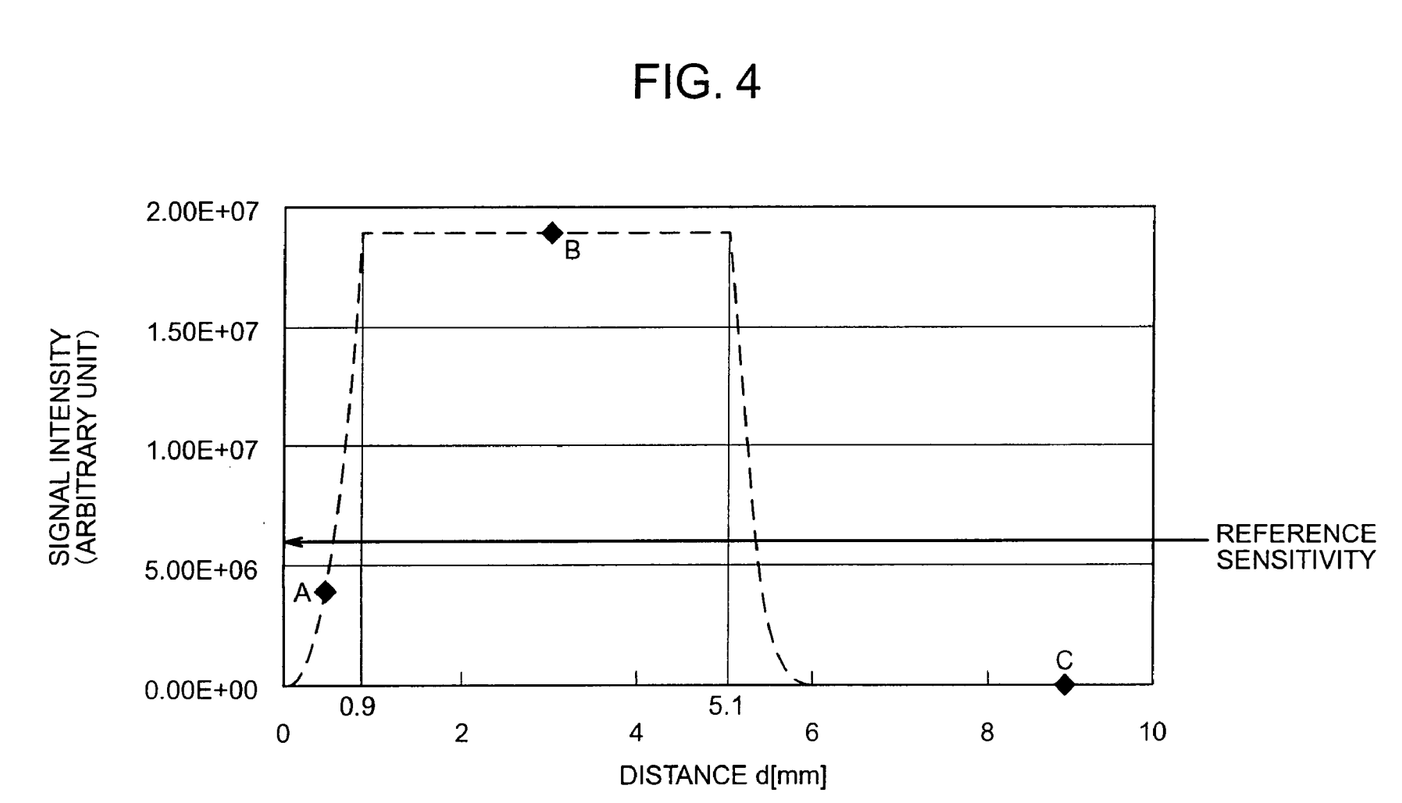
FIG. 4 is a diagram showing a measurement result of the change of the signal intensity by the sample ion detected when the distance between the center of the aperture 12 at the end of the GC column 9 and the axis indicated by one-dot-chain line in FIGS. 1 and 2 is kept constant and the center position of the aperture 12 at the end of the GC column 9 is changed in the direction of the axis indicated by one-dot-chain line in FIGS. 1 and 2 in the construction of the first embodiment.

FIG. 4 shows the measurement result of the change (sensitivity change) of the signal intensity (in arbitrary unit) by the sample ion detected when the center position of the aperture 12 at the end of the GC column 9 is changed in the direction of the axis indicated by one-dot-chain line while the distance between the center of the aperture 12 at the end of the GC column 9 and the axis indicated by one-dot-chain line in FIGS. 1 and 2 is kept constant at r=1 mm. In other words, FIG. 4 shows the change of the signal intensity due to the sample ion detected when the distance d (see FIG. 2) of the center position of the aperture 12 at the end of the GC column 9 from the ion inlet of the sample ion introduction aperture 8 is changed. The measurement condition is the same as that of FIG. 3.

The primary ion generation gas is caused to flow at a flow rate of 1,000 mL/min through the primary ion generation gas introduction piping 1, the primary ion generation gas is exhausted at a flow rate of 350 mL/min from the sample ion introduction aperture 8 and the primary ion generation gas is exhausted at a rate of 650 mL/min from the primary ion introduction aperture 11.

The point A shown in FIG. 4 represents the signal intensity (in arbitrary unit) due to the sample ion detected when the center position of the aperture 12 at the end of the GC column 9 is arranged extremely close to the sample ion movement aperture 8 and the distance is set to d=0.5 mm. When d=0.5 mm, the sample gas flowing out from the aperture 12 at the end of the GC column 9 is almost fully introduced into the sample ion movement aperture 8.

The point B shown in FIG. 4 represents the signal intensity (in arbitrary unit) due to the sample ion detected when the center position of the aperture 12 at the end of the GC column 9 is arranged at the intermediate position substantially equidistant from the center of the ion output of the primary ion introduction aperture 11 and from the center of the ion inlet of the sample ion movement aperture 8 and the distance is set to d=3 mm. When d=3 mm, about a half of the flow rate of the sample gas flowing out from the aperture 12 at the end of the GC column 9 is exhausted from the sample ion introduction aperture 8 and the flow rate of the remaining gas is exhausted from the primary ion introduction aperture 11.

The point C in FIG. 4 represents the signal intensity (in arbitrary unit) by the sample ion detected at d=9 mm when the center of the aperture 12 at the end of the GC column 9 is arranged at a position inside the first ionization portion 3 between the center of the primary ion introduction aperture 11 and the center of the distal end of the needle electrode 10. When d=9 mm, the flow rate of the sample gas flowing though the aperture 12 at the end of the GC column 9 is exhausted substantially fully from the primary ion generation gas exhaust piping 7. In comparison with the reference sensitivity, the sensitivity can be improved 3.2 times at the point B in FIG. 4. The sensitivity is 0.7 times at the point A and is 0.1 times at the point C and is lower than the reference sensitivity. It has been confirmed from this result that the higher sensitivity than the reference sensitivity can be obtained when the center of the aperture 12 at the end of the GC column 9 is arranged at the intermediate position substantially equidistant from the center of the ion outlet of the primary ion introduction aperture 11 and from the center of the ion inlet of the reference ion movement aperture 8.

When $A'=A\times\sigma\times I\times\sigma\times$(signal intensity)/(number of sample ions) is put in Expression (1), the following Expression (6) can be obtained.

$$\text{(signal intensity)} = A' \times \text{reaction time } (T) \quad \text{expression (6)}$$

Here, the point A shown in FIG. 4 is close to the sample ion movement aperture 8 and the following Expression (7) can be assumed.

$$T \approx T_8 = (2\pi d^3)/(3Q_8) \quad \text{expression (7)}$$

When the condition of the point A (d=0.5 mm, $Q_8$=350 mL/min, signal intensity=4E+6) is put, A'=8.0E+9. Because the sensitivity at the point A (d=0.5 mm) is 0.7 times the reference sensitivity, the position at which the sensitivity equal to the reference sensitivity is obtained is given as d=0.6 mm from Expressions (6) and (7).

Similarly, the position close to the primary ion introduction aperture 11 at which the sensitivity equal to the reference sensitivity is obtained is given as d=5.4 mm by putting L=6 mm, $Q_{11}$=650 mL/min and A=8.0E+9 into (6) by regarding Expression (6) as (8):

$$T \approx T_{11} = (2\pi(L-d)^3)/(3Q_{11}) \quad \text{expression (8)}$$

The sample gas introduced from the aperture 12 at the end of the GC column 9 is exhausted half and half at the point B shown in FIG. 4 from the primary ion introduction aperture 11 and from the sample ion movement aperture 8. Therefore, the reaction time can be regarded as the mean value of $T_8$ and $T_{11}$. When d=3 mm is put into Expressions (6), (7) and (8), the signal intensity=1E+9 can be obtained. Though this value does not agree with the experimental value shown in FIG. 4, the reaction can be regarded as having proceeded sufficiently and got into saturation.

FIG. 4 shows by dotted line the relation between the distance d and the signal intensity acquired from the result described above. Because the reaction has got into saturation within the range of 0.9 mm≦d≦5.1 mm, the signal intensity does not rise any more.

The flow velocity ratio obtained from the velocity vectors $V_8$ and $V_{11}$ when the position of the aperture 12 at the end of the outlet of the GC column 9 is arranged at d=0.9 mm is $V_8:V_{11}\approx18:1$. Assuming that the flow rate Q of the gas introduced from the aperture 12 at the end of the outlet of the GC column 9 is distributed in accordance with this flow velocity ratio and is exhausted from the sample ion movement aperture 8 and from the primary ion introduction aperture 11, the flow rate Q' exhausted from the sample ion movement aperture 8 is given by Q'≈0.95Q. Similarly, when the aperture 12 is arranged at d=5.1 mm, Q' is given by Q'≈0.02Q.

To sum up, the end 12 of the outlet of the GC column 9 is preferably arranged at the position that satisfies the relation 0.02Q≦Q'≦0.95Q for the flow rate Q' of the sample gas Q exhausted from the sample ion movement aperture 8.

Particularly when sample components having a small collision cross section and a long reaction time till saturation are ionized, regulation is made so that Q' becomes substantially equal to about 0.5Q. The equation Q'=0.5Q can be satisfied when the center of the aperture 12 at the end of the GC column 9 is arranged at the intermediate position substantially equidistant from the center of the ion outlet of the primary ion introduction aperture 11 and from the center of the ion inlet of the sample ion movement aperture 8, more accurately at the position at which the flow velocity $V_8$ is substantially equal to the flow velocity $V_{11}$ obtained from Expressions (2) and (3). In this case, the reaction time $T_8$ or $T_{11}$ obtained from Expression (4) or (5) becomes sufficiently long and the reaction time in which the primary ion and the sample molecule coexist can be sufficiently extended in the field of the ion-molecule reaction, the generation amount of the sample ion can be increased and the sensitivity can be improved. Incidentally, when the relation 0.4Q≦Q'≦0.6Q is substantially satisfied, a similar effect can be obtained.

In other words, Q'≈0.5Q can be satisfied when the center of the aperture 12 at the end of the GC column 9 is arranged at the intermediate position substantially equidistant from the center of the ion outlet of the primary ion introduction aperture 11 and from the center of the ion inlet of the sample ion movement aperture 8. When Q'≈0.5Q is satisfied, the sample gas introduced from the aperture 12 at the end of the GC column 9 is exhausted with good balance from the primary ion introduction aperture 11 and from the sample ion movement aperture 8. Consequently, the retention time in which the primary ion and the sample molecule coexist in the field of the ion-molecule reaction can be sufficiently extended, the sufficient time for the progress of the ion-molecule reaction can be secured, the generation amount of the sample ion can be increased and the sensitivity can be improved.

Second Embodiment

Figure 5:
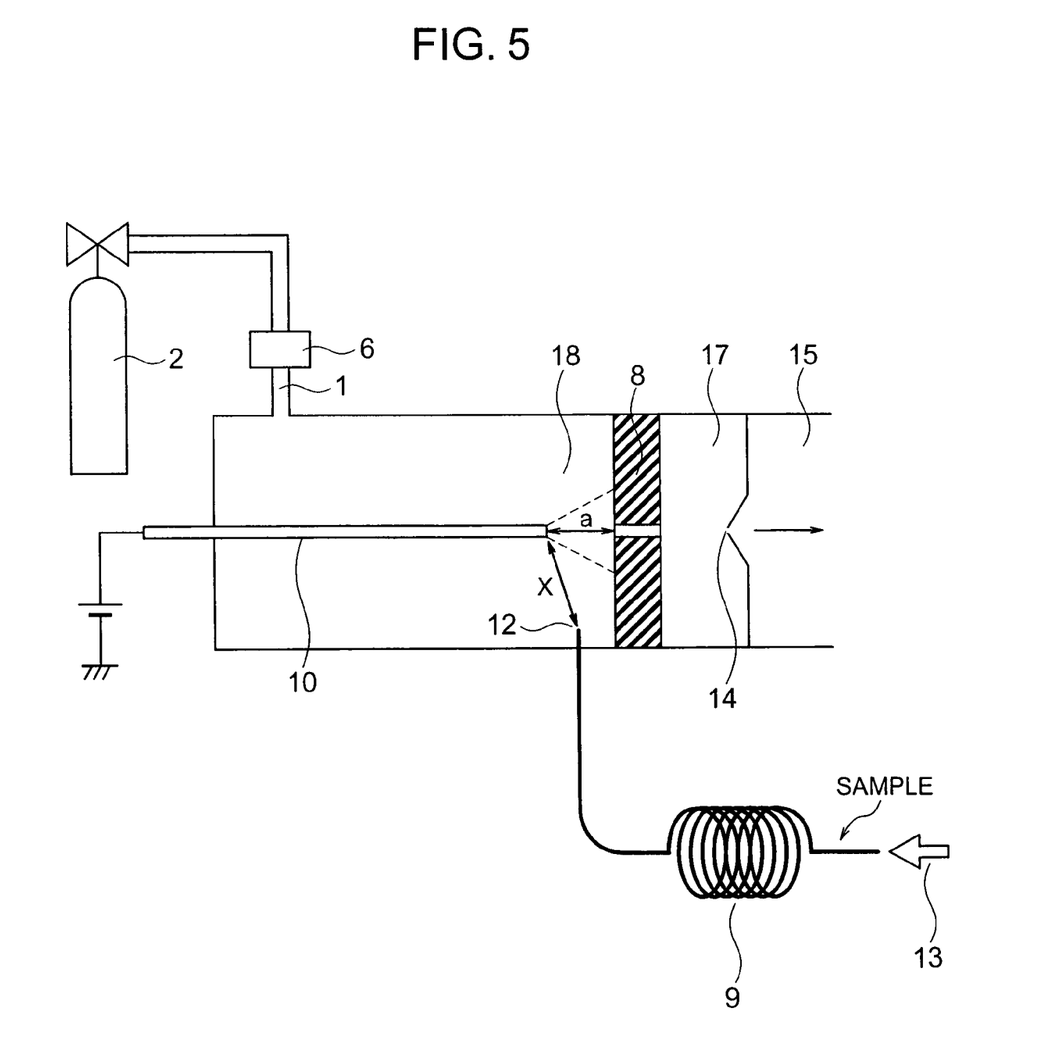
FIG. 5 is a sectional view showing a construction of a mass spectrometer according to a second embodiment of the invention.

FIG. 5 is a sectional view showing a construction of a mass spectrometer according to the second embodiment of the invention. The construction of the second embodiment is effective for executing positive ionization of the sample gas.

In the second embodiment, the sample gas introduced from the aperture 12 at the end of the GC column 9 is introduced into a corona discharge portion (area indicated by dotted line in FIG. 2). The needle electrode 10 is arranged inside the ionization portion 18 and the primary ion generation gas introduction piping 1 is connected at a position far from the sample ion movement aperture 8 (position on the root side of needle electrode 10) on the opposite side to the tip end of the needle electrode 10 inside the ionization portion 18. The primary ion generation gas from the gas cylinder 2 is introduced through the primary ion generation gas introduction piping 1 into the ionization portion 18 while its flow rate is regulated by the mass flow controller 6.

In the second embodiment, the center of the aperture 12 at the end of the GC column 9 is arranged at a position at which the sample gas from the aperture 12 at the end of the GC column 9 is introduced into the corona discharge portion. When the aperture 12 at the end of the GC column 9 is disposed at this time inside the corona discharge portion, corona discharge cannot be induced stably or the resulting sample ion adheres to the aperture 12 at the end of the GC column to lower the sensitivity. Therefore, the center of the aperture 12 at the end of the GC column 9 is preferably arranged at the position satisfying the relation $x \geq a$ between the center of the distal end of the needle electrode 10 and the center of the ion inlet of the sample ion movement aperture 8. Here, symbol $a$ represents the distance between the center of the tip end of the needle electrode 10 and the center of the ion inlet of the sample ion movement aperture 8 and symbol x represents the distance between the center of the tip end of the needle electrode 10 and the center of the aperture 12 at the end of the GC column 9.

In the second embodiment, the primary ion generation gas and the sample gas are exhausted from only the sample ion movement aperture 8. Therefore, the full amount of the primary ion generation gas and the full amount of the sample gas introduced from the aperture 12 at the end of the GC column 9 are exhausted from the sample ion movement aperture 8 to the differential exhaust portion 17. In consequence, the sum of the primary ion generation gas and the introduction amount of the sample gas into the ionization portion 18 is equal to the gas amount exhausted from the sample ion movement aperture 18. Because the sample gas is not exhausted from the ionization portion 18 through exhaust ports other than the ion movement aperture 8, the amount of the sample gas exhausted without reacting with the primary ion becomes small and the sensitivity can be improved.

Assuming that the gas flow rate passing through the sample ion movement aperture 8 is 350 mL/min, the sample gas flow rate introduced from the aperture 12 at the end of the GC column 9 is 4 mL/min and 100% of the sum of the introduction amount of the primary ion generation gas and the introduction amount of the sample gas is exhausted from the sample ion movement aperture 8, the introduction amount of the primary ion generation gas is 346 mL/min and the dilution ratio of the sample gas inside the ionization portion 18 becomes lower than in the construction shown in FIG. 1. Therefore, this construction is effective when contamination of the ion source by impurities is small.

To reduce contamination by the impurities inside the ionization portion 18, it is advisable to increase the flow rate of the primary ion generation gas and to dilute the sample gas in the proximity of the corona discharge portion. To conduct measurement while the internal pressure of the ionization portion 18 is kept at the atmospheric pressure, however, it is necessary to exhaust the mixed gas of the primary ion generation gas and the sample gas from the ionization portion 18 in the amount corresponding to the increment of the flow rate of the primary ion generation gas through an exhaust port separately from the sample ion movement aperture 8. This exhaust port is preferably formed in the wall of the ionization portion 18 in the proximity of the corona discharge portion of the ionization portion 18 and in the proximity of the sample ion movement aperture 8 such as the wall in the direction perpendicular to the needle electrode 10 and intersecting at right angles the partition forming the sample ion movement aperture 8. When the flow rate of the primary ion generation gas is increased, however, the proportion of the sample gas that is diluted by the primary ion generation gas increases and the sensitivity drops.

Therefore, when the different exhaust port (not shown) is separately formed from the sample ion movement aperture 8 in the ionization portion 18, at least 80% of the sum of the introduction amount of the primary ion generation gas and that of the sample gas is preferably exhausted from the sample ion movement aperture 8.

Under such a condition, the proportion of the sample gas flowing along the portion near the axis connecting the distal end of the needle electrode and the center of the ion inlet of the sample ion movement aperture 8 at which the primary ion and the sample gas (molecule) efficiently react with each other occupies at least 80% of the full amount introduced into the ionization portion 18 and the measurement can be carried out while the sensitivity of 80 to 100% is maintained in comparison with the case where the full amount introduced into the ionization portion 18 is caused to flow along the portion near the axis connecting the tip end of the needle electrode 10 and the center of the ion inlet of the sample ion movement aperture 8.

In the construction of the second embodiment, the tip end of the needle electrode 10, the center of the sample ion movement aperture 8 and the center of the ion introduction aperture 14 are arranged on the same axis but they can be arranged while deviating from one another. When they are arranged in deviation, it is possible to prevent the neutral molecule from mixing into the mass analysis portion 15 and to reduce the noise resulting from the neutral molecule. In either case, the resulting sample ion is introduced into the mass analysis portion 15 through the sample ion movement aperture 8 and the ion introduction aperture 14.

Third Embodiment

Figure 6:
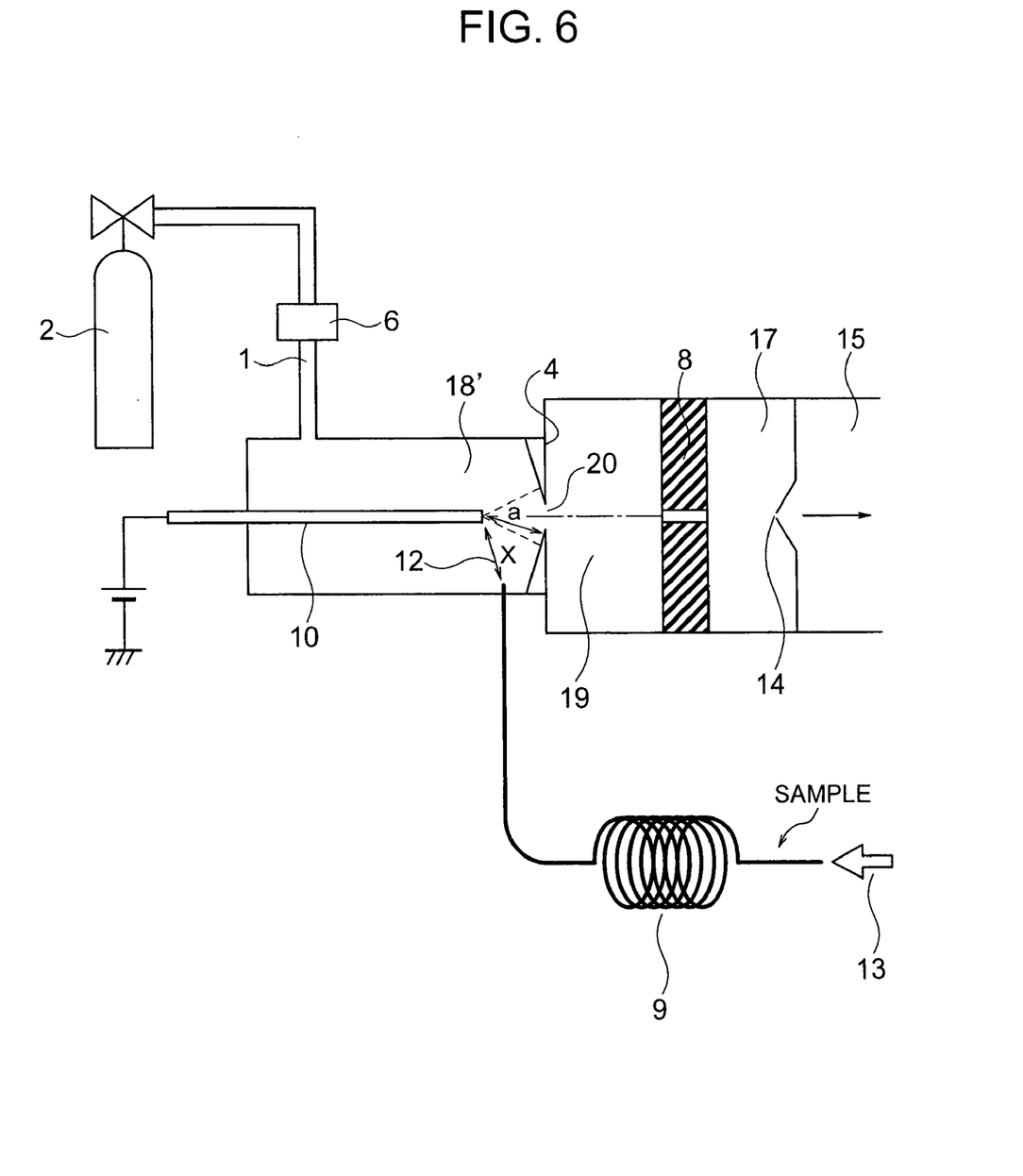
FIG. 6 is a sectional view showing a construction of a mass spectrometer according to a third embodiment of the invention.

FIG. 6 is a sectional view showing a construction of a mass spectrometer according to the third embodiment of the invention. The construction of the third embodiment is effective for executing positive ionization of the sample components having a small reaction rate constant in the ionization reaction.

The difference of the third embodiment from the first embodiment resides in the arrangement position of the center of the aperture 12 at the end of the GC column 9, the arrangement position of the primary ion generation gas introduction piping 1 and exhausting of the gas from an ion passage aperture 20 in place of the primary ion generation gas exhaust piping 7. In the third embodiment, the sample gas introduced from the aperture 12 at the end of the GC column 9 is introduced into the corona discharge portion (area indicated by dotted line in FIG. 6) in the same way as in the second embodiment.

The ionization portion 18' in which the needle electrode 10 is arranged is connected to an ion movement space (area into which primary ion generation gas is introduced) 19 through the lead-out electrode 4 in which the ion passage aperture 20 is formed. The ion movement space 19 is connected to the differential exhaust portion 17 through a partition in which the sample ion movement aperture 8 is formed. The primary ion generation gas from the gas cylinder 2 is introduced through the primary ion generation gas introduction piping 1 into the ionization portion 18' at the position opposite to the tip end of the needle electrode 10 and far from the ion passage aperture 20 (position on the root side of needle electrode 10) while its flow rate is regulated by the mass flow controller 6. The primary ion generation gas introduced into the ionization portion 18' is introduced into the ion movement space 19 together with the sample gas, the primary ion and the sample ion generated in the ionization portion 18' through the ion passage aperture 20 and is exhausted from the differential exhaust portion 17.

In the third embodiment, the center of the aperture 12 at the end of the GC column 9 is arranged at a position at which the sample gas from the aperture 12 at the end of the GC column 9 is introduced into the corona discharge portion.

When the aperture 12 at the end of the GC column 9 is disposed at this time inside the corona discharge portion, corona discharge cannot be induced stably or the resulting sample ion adheres to the aperture 12 at the end of the GC column to lower the sensitivity. Therefore, the center of the aperture 12 at the end of the GC column 9 is preferably arranged at the position satisfying the relation x≧a between the center of the tip end of the needle electrode 10 and the center of the ion inlet of the ion passage aperture 20. Here, symbol $\underline{a}$ represents the distance between the center of the tip end of the needle electrode 10 and the center of the ion inlet of the ion passage aperture 20 and symbol x represents the distance between the center of the distal end of the needle electrode 10 and the center of the aperture 12 at the end of the GC column 9.

To secure a longer retention time in which the primary ion and the sample molecule coexist, the relation z≧a is preferably satisfied. Here, symbol $\underline{a}$ represents the distance between the center of the tip end of the needle electrode 10 and the center of the ion inlet of the ion passage aperture 20 and symbol z represents the distance between the center of the ion outlet of the ion passage aperture 20 and the center of the ion inlet of the sample ion movement aperture 8.

The sample gas introduced into the corona discharge portion passes through the ion passage aperture 20 and is introduced into the ion movement space 19. The sample ion is generated by the ion-molecule reaction between the primary ion generated by corona discharge inside the corona discharge portion and the sample molecule. The sample ion is also generated by the ion-molecule reaction between the primary ion and the sample gas passing through the ion passage aperture 20. As a result, the retention time for the coexistence of the primary ion and the sample molecule can be secured in both corona discharge portion and ion movement space 19, the sufficient time for the progress of the ion-molecule reaction can be secured, the generation amount of the sample ion can be increased and the sensitivity can be improved.

In the third embodiment, at least 80% of the sum of the introduction amount of the primary ion generation gas and that of the sample gas is preferably exhausted from the sample ion movement aperture 8 even when an exhaust port (not shown) is disposed separately from the primary on generation gas exhaust piping 7 in the ionization portion 18' or the ion movement space 19 in the same way as in the second embodiment.

Under such a condition, the proportion of the sample gas flowing along the portion near the axis connecting the tip end of the needle electrode 10 and the center of the ion inlet of the sample ion movement aperture 8 at which the primary ion and the sample gas (molecule) efficiently react with each other occupies at least 80% of the full amount introduced into the ionization portion 18 and the measurement can be carried out while the sensitivity of 80 to 100% is maintained in comparison with the case where the full amount introduced into the ionization portion 18 is caused to flow along the portion near the axis connecting the distal end of the needle electrode 10 and the center of the ion movement aperture 8 in the same way as in the second embodiment.

In the second embodiment shown in FIG. 5, the sample gas is directly exhausted from the corona discharge portion to the sample ion movement aperture 8. Therefore, when a sample having a low reaction rate constant in the ionization reaction is ionized, the retention time in which the primary ion and the sample molecule coexist cannot be secured sufficiently and the generation amount of the sample ion cannot be increased. In this case, the third embodiment having the ion movement space 19 can conduct the analysis at a higher sensitivity than in the second embodiment.

In the construction of the third embodiment, the tip end of the needle electrode 10, the center of the ion passage aperture 20, the center of the sample ion movement aperture 8 and the center of the ion introduction aperture 14 are arranged on the same axis but they can be arranged while deviating from one another. When they are arranged in deviation, it is possible to prevent the neutral molecule from mixing into the mass analysis portion 15 and to reduce the noise resulting from the neutral molecule. In either case, the resulting sample ion is introduced into the mass analysis portion 15 through the ion passage hole 20, the sample ion movement aperture 8 and the ion introduction aperture 14.

Figure 7:
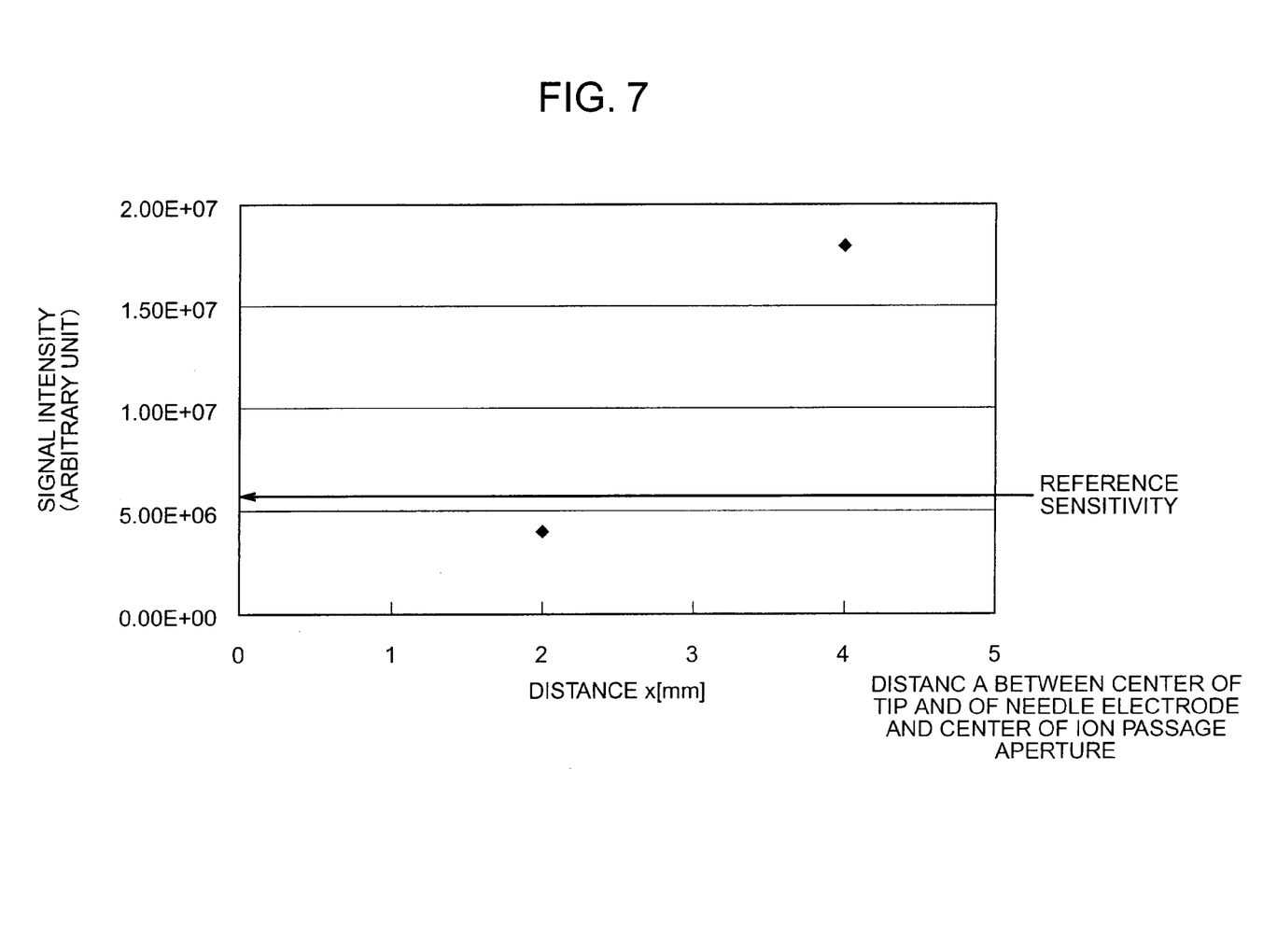
FIG. 7 is a diagram showing a measurement result of a change of a signal intensity by a sample ion detected when a distance between the center of the aperture 12 at the end of the GC column 9 and the center of a tip end portion of a needle electrode 10 is changed in the construction of the third embodiment.

FIG. 7 shows the measurement result of the change (sensitivity change) of the signal intensity (in arbitrary unit) by the sample ion that is detected when the distance x between the center of the aperture 12 at the end of the GC column 9 and the center of the tip end of the needle electrode 10 is changed. The measurement condition is the same as the condition used for obtaining the result shown in FIG. 3.

The distance $\underline{a}$ between the center of the tip end of the needle electrode 10 and the center of the ion inlet of the ion passage aperture 20 is a=3.5 mm, the distance z between the center of the ion outlet of the ion passage aperture 20 and the center of the ion inlet of the sample ion movement aperture 8 is z=6 mm, and $\underline{a}$ and z satisfy the relation z≧a. The primary ion generation gas is caused to flow at a flow rate of about 350 mL/min through the primary ion generation gas introduction piping 1 and the full amount of the primary ion generation gas and the full amount of the sample gas from the aperture 12 at the end of the GC column 9 are exhausted from the differential exhaust portion 17 through the ion passage aperture 20 and the sample ion movement aperture 8.

The sensitivity at x=2 mm when x≦a is 0.7 times the reference sensitivity and is lower than the reference sensitivity but the sensitivity at x=4 mm when x≧a is trice the reference sensitivity.

Incidentally, it is possible to connect the outlet at the other end opposite to one end (inlet) of the GC column 9 through which the sample (mixed sample) is introduced with the carrier gas 13 to one of the ends of the sample gas piping and to use the outlet at the other end of this sample gas piping in place of the aperture 12 at the end of the GC column 9 in the first, second and third embodiments.

In other words, it is possible in the embodiment shown in FIGS. 1 and 2 to connect the other end of the GC column and the second ionization portion 5 by the sample gas piping, to arrange the outlet at the other end of the sample gas piping to the center position of the aperture 12 at the other end of the GC column 9 shown in FIGS. 1 and 2, to connect the other end of the GC column 9 and the ionization portion 18, 18' by the sample gas piping in the embodiment shown in FIG. 5 and in the third embodiment shown in FIG. 6, and to arrange the outlet at the other end of the sample gas piping to the center position of the aperture 12 at the end of the GC column 9 shown in FIGS. 5 and 6. In these constructions, the inner diameter of the sample gas piping may be the same as the inner diameter of the GC column.

The invention can provide the mass spectrometer (GC/APCI/MS) and the mass spectrometry method that separate the mixed sample by GC, ionize the sample gas so separated by using the APCI source having the construction that does not easily invite contamination and can be applied to mixed samples of a broad application field without being affected by dilution of the sample gas by the primary ion generation gas.

It should be further understood by those skilled in the art that although the foregoing description has been made on embodiments of the invention, the invention is not limited thereto and various changes and modifications may be made without departing from the spirit of the invention and the scope of the appended claims.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A mass spectrometer comprising:
an atmospheric pressure chemical ionization (APCI) source including:
(a1) a first ionization portion including a needle electrode to which a voltage for corona discharge is applied, and an exhaust aperture for said primary ion generation gas, for generating a primary ion from said primary ion generation gas by discharge of said needle electrode;
(a2) a primary ion introduction aperture through which said primary ion flows; and
(a3) a second ionization portion including an introduction aperture of said primary ion generation gas, for generating a sample ion of a sample gas by the reaction between said primary ion introduced from said primary ion introduction aperture and said sample gas introduced from an end of a column of gas chromatography, said second ionization portion having the end of said column arranged therein;
(b) a sample ion movement aperture through which said sample ion moves; and
(c) a mass analysis portion for conducting mass analysis of said sample ion; wherein:
said exhaust aperture is arranged at a portion on the opposite side to the tip end of said needle electrode, said primary ion generation gas introduced into said second ionization portion is caused to flow to said exhaust aperture from the distal end of said needle electrode through said primary ion introduction aperture, and the end of said column is arranged at a position satisfying the relation $r \leq 2R$ where R is a radius of an inner diameter of said primary ion introduction aperture and r is a distance between an axis connecting the center of said primary ion introduction aperture and the center of said sample ion movement aperture, and end of said column.

2. A mass spectrometer as defined in claim 1, which satisfies the relation $0.02Q \leq Q' \leq 0.95Q$ where Q is the flow rate of said sample gas at the end of said column and Q' is the flow rate of said sample gas introduced into said second ionization portion and exhausted from said sample ion movement aperture.

3. A mass spectrometer as defined in claim 1, which satisfies the relation $0.4Q \leq Q' \leq 0.6Q$ where Q is the flow rate of said sample gas at the end of said column and Q' is the flow rate of said sample gas introduced into said second ionization portion and exhausted from said sample ion movement aperture.

4. A mass spectrometer as defined in claim 1, wherein said sample ion moving in said sample ion movement aperture is introduced into said mass analysis portion through a differential exhaust portion.

5. A mass spectrometer as defined in claim 1, which includes a sample gas piping connected to the end of said column, and wherein the end of said sample gas piping is arranged inside said second ionization portion in place of the end of said column disposed inside said second ionization portion.

6. A mass spectrometer comprising:
(a) an atmospheric pressure chemical ionization (APCI) source including a needle electrode to which a voltage for corona discharge is applied, and an ionization portion having a primary ion generation gas introduction aperture, for generating a primary ion from said primary ion generation gas by discharge of said needle electrode, having an end of a column of gas chromatography disposed therein, and generating a sample ion of a sample gas by the reaction between said sample gas introduced from the end of said column and said primary ion;
(b) a sample ion movement aperture through which said sample ion moves; and
(c) a mass analysis portion for conducting mass analysis of said sample ion;
wherein the end of said column is arranged at a portion between the tip end of said needle electrode and said sample ion movement aperture.

7. A mass spectrometer as defined in claim 6, wherein the end of said column is arranged at a position satisfying the relation $x \geq a$ where $\underline{a}$ is a distance between the center of a tip end of said needle electrode and the center of an ion inlet of said sample ion movement aperture and x is a distance between the center of the tip end of said needle electrode and an aperture at the end of said column.

8. A mass spectrometer as defined in claim 6, which includes a sample gas piping connected to the end of said column, and wherein the end of said sample gas piping is arranged inside said atmospheric pressure chemical ionization (APCI) source in place of the end of said column.

9. A mass spectrometer as defined in claim 6, wherein said sample ion moving in said sample ion movement aperture is introduced into said mass analysis portion through a differential exhaust portion.

10. A mass spectrograph comprising:
an atmospheric pressure chemical ionization (APCI) source including:
(a1) an ionization portion including a needle electrode to which a voltage for corona discharge is applied, and a primary gas generation gas introduction aperture, generating a primary ion from said primary ion generation gas by discharge of said needle electrode, having a column of gas chromatography disposed therein and generating the sample ion of said sample gas by the reaction between said sample gas introduced from an end of said column and said primary ion;
(a2) an ion passage aperture through which said sample ion, said primary ion, said primary ion generation gas and said sample gas flow; and
(a3) an area into which said sample ion, said primary ion, said primary ion generation gas and said sample gas are introduced through said ion passage aperture;
(b) a sample ion movement aperture through which said sample ion moves; and
(c) a mass analysis portion for conducting mass analysis of said sample ion;
wherein the end of said column is arranged between the tip end of said needle electrode and said ion passage aperture.

11. A mass spectrometer as defined in claim 10, wherein the end of said column is arranged at a position satisfying the relation x≧a where a is a distance between the center of a tip end of said needle electrode and the center of an ion inlet of said sample ion movement aperture and x is a distance between the center of the tip end of said needle electrode and an aperture at the end of said column.

12. A mass spectrometer as defined in claim 10, wherein said sample ion moving through said sample ion movement aperture is introduced into said mass analysis portion through a differential exhaust portion.

13. A mass spectrometer as defined in claim 10, which includes a sample gas piping connected to the end of said column, and wherein the end of said sample gas piping is arranged inside said atmospheric pressure chemical ionization (APCI) source in place of the end of said column.

* * * * *